(12) United States Patent
Martti

(10) Patent No.: US 6,744,847 B2
(45) Date of Patent: Jun. 1, 2004

(54) METHOD AND APPARATUS FOR PANORAMIC DENTAL X-RAYING

(75) Inventor: Juhani Martti, Helsinki (FI)

(73) Assignee: Instrumentarium Corporation, Helsinki (FI)

( * ) Notice: Subject to any disclaimer, the term of this patent is extended or adjusted under 35 U.S.C. 154(b) by 287 days.

(21) Appl. No.: 09/900,524

(22) Filed: Jul. 6, 2001

(65) Prior Publication Data

US 2002/0048342 A1 Apr. 25, 2002

(30) Foreign Application Priority Data

Jul. 7, 2000 (FI) .............................. 20001620

(51) Int. Cl.⁷ ............................. A61B 6/14
(52) U.S. Cl. .......................... 378/39; 378/38
(58) Field of Search ................ 378/38, 39, 1, 378/168

(56) References Cited

U.S. PATENT DOCUMENTS 4,521,899 A   6/1985  Finkenzeller et al. ......... 378/40
4,741,007 A * 4/1988  Virta et al. .................... 378/39
4,783,793 A * 11/1988 Virta et al. .................... 378/39

FOREIGN PATENT DOCUMENTS

| EP | 0236790 | 2/1987 |
| EP | 0632995 | 6/1994 |
| FI | 802988  | 9/1980 |
| FI | 812954  | 9/1981 |

* cited by examiner

Primary Examiner—Craig E. Church
Assistant Examiner—Jurie Yun
(74) Attorney, Agent, or Firm—Ware, Fressola, Van Der Sluys & Adolphson LLP

(57) ABSTRACT

A method and an apparatus for panoramic dental X-raying comprises an arm (7) rotating about an axis (6), a radiation source (9) at one end (8) of the arm for generating an X-ray beam (12), a shutter (13) for shaping the X-ray beam, and at the opposite end (10) of the arm, a recorder (11) for receiving the X-ray beam after it has passed through the dental arch for forming an image of the dental arch. The X-raying is performed with rotation of the arm (7) so as to image substantially the entire length of the dental arch. The shutter (13) narrows the X-ray beam (12) in the front area of the dental arch in order to increase the thickness of the sharply imaged layer compared to the two sides of the dental arch.

9 Claims, 5 Drawing Sheets

METHOD AND APPARATUS FOR PANORAMIC DENTAL X-RAYING

TECHNICAL FIELD

This invention relates to a method for panoramic dental X-raying, in which the beam of rays emitted from a radiation source mounted on a rotating arm is guided through the dental arch to a recorder located in the arm opposite the radiation source in order to form an image, and in which the arm is rotated so as to form an image of essentially the entire length of the dental arch. The invention also relates to an apparatus for implementing said method.

BACKGROUND OF THE INVENTION

Panoramic X-raying aims at forming images of the teeth in a projection that is as orthogonal, i.e. perpendicular as possible, thus avoiding having the teeth imaged in an overlapping manner. Since the dental arch differs in shape from a circular arch, the axis of rotation of the arm must be shifted in course of the imaging in order to achieve the purpose of orthogonal imaging. The radius of curvature of the dental arch being smallest in the front area of the arch, it is preferred to approach the axis of rotation to the teeth when this area is imaged in order to minimise the need for shifting the axis. During X-raying of the molar teeth, the distance between the axis and the spot of the teeth to be imaged is typically longer.

Due to the short distance between the axis of rotation of the arm and the spot of the teeth to be imaged in the front area of the dental arch, the sharply imaged teeth layer will be narrow in this area. In terms of imaging geometry, the spots located in a single plane through which the beam of rays penetrates each time will be projected as spots to the recorder. Beyond this plane, the spots covered by the beam of rays will be projected as elongated lines to the recorder, and the thickness of the "sharp" layer on either side of the plane is determined by the degree of extension considered acceptable. Generally a 0.6 mm blur is used as the limit of the sharp layer, blur implying the spot extension divided by the ratio of enlargement.

A narrow sharp layer, i.e. a thin layer in the front area of the dental arch, involves a drawback, since the teeth position divergence is highest precisely in this area. If the teeth are not included in the sharp layer, but will be located more or less outside this, the X-raying has failed. There is thus a need to compensate for this drawback so as to achieve increased probability of successful images and to reduce the need for repeated X-raying sessions, which would expose the patient to additional radiation.

SUMMARY OF THE INVENTION

The object of the invention is thus to provide a solution for eliminating the drawback of current panoramic X-raying techniques mentioned above. The invention comprises limiting the X-ray beam by a shutter in the front area of the dental arch as compared to the two sides of the arch, in order to increase in said front area the thickness of the layer of which a sharp image is formed, and retarding the movement of the X-ray beam in said front area of the dental arch compared to the two sides of the arch.

The invention is based on imaging geometry, in which the thickness of a sharply imaged layer is inversely proportional to the width of the beam of rays on the recorder. Should the beam be infinitely narrow, it would form an infinitely thick image, in other words, all the objects located between the source of radiation and the recorder would be imaged with equal sharpness. Inversely, the broader the beam of rays, the narrower the sharply imaged layer between the source of radiation and the recorder. In the practice, the beam of rays obtained from the source of radiation has a finite width, and by adjusting this width under control with the shutter in accordance with the invention, the invention allows compensation for the decreased thickness of the sharp layer that would occur in the front area of the dental arch if no adjustment were performed.

In accordance with the invention, the increased thickness of the sharp layer in the front area of the dental arch facilitates the positioning of the patient, provides higher probability of successful images and reduces the exposure to radiation of the patients. It is particularly notable that the increased layer thickness provides enhanced visibility of the dental structures, such as the root tips, in the pictures.

An adjustable shutter of X-ray beams is not novel per se, but has been disclosed i.a. by FI lay-out print 64999 (Patent Application 802,988) and FI Patent Application 812,954. However, these references do not describe the use of a shutter with a view to decrease to thickness of the sharp layer in the front area of the teeth, as in the present invention.

As it has appeared above, there is a need for compensating for the narrowed sharp layer in the front area of the dental arch especially in such panoramic X-raying applications where the axis of rotation of the arm is shifted during the imaging session so that the distance between the axis and the imaged spot of the dental arch, i.e. the "radius of imaging" is shortest in the front area of the arch. In this area, the X-ray beam penetrates the dental arch substantially perpendicularly. The solution to this is to limit the X-ray beam as in the invention on either side of the central normal to the arch in a sector with a central angle of e.g. approx. 60–80°, preferably about 70°.

In accordance with the invention, the X-ray beam is narrowed in the front area of the dental arch preferably so as to obtain an at least 50% increase of the thickness of the sharp layer. The layer thickness of the sharp layer will preferably be about 1.5 cm or more in the front area of the arch. With current panoramic X-raying methods, involving a short imaging radius in the front area of the dental arch, the thickness of the sharp layer is typically of the order of magnitude of about 1 cm or even less, without the compensation of the invention.

Since a narrower X-ray beam decreases the radiation impinging on the recorder, in order to achieve adequate exposure, it is necessary to retard the movement of the X-ray beam in the front area of the dental arch relative to the two sides of the arch. In this connection, the movement of the beam refers to the speed. The beam is moved or scanned along the dental arch in a direction transverse to the radiation direction. In the practice, the retardation can be of the order of about 40%–60%, preferably about 50%. By these means, a substantially homogeneous dark tone of the image is available over the entire length of the dental arch.

Since, in the practice, it is desirable to X-ray the dental arch with one single continuous rotational movement, the X-ray beam is limited in accordance with the invention as the movement reaches the front area of the dental arch, and after this the beam is accordingly enlarged to its original width as it leaves this area. It is thus preferable to connect the adjustment of the shutter with the movement performed during the imaging, for instance by narrowing and widening the shutter aperture through which the X-ray beam passes under mechanical control of the movement of the axis of rotation of the arm. Retardation and subsequent acceleration of the movement of the X-ray beam would take place in tandem with the gradual narrowing and widening of the shutter to ensure a substantially constant exposure of the arch to X-rays through the entire length of the arch.

The apparatus of the invention for panoramic dental X-raying, which comprises an arm rotating about an axis, a radiation source at one end of the arm for emitting an X-ray beam, a shutter shaping the X-ray beam, and a recorder placed at the opposite end of the arm to receive the X-ray beam after it has passed through the dental arch for forming an image of the dental arch, is characterised by the shutter comprising an aperture through which the X-ray beam passes and which is disposed to decrease in width during the rotational movement of the arm and to subsequently resume its original width. The adjustment of this aperture is preferably performed under mechanical control by the arm rotating mechanism.

BRIEF DESCRIPTION OF THE DRAWINGS

The invention is explained in further detail below with reference to the accompanying drawings, in which.

Figure 1:
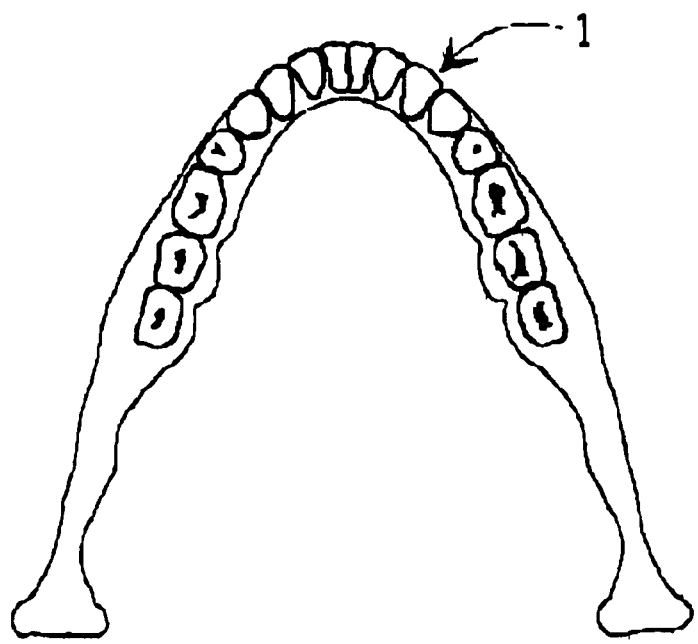
FIG. 1 shows the dental arch with the teeth
Figure 2:
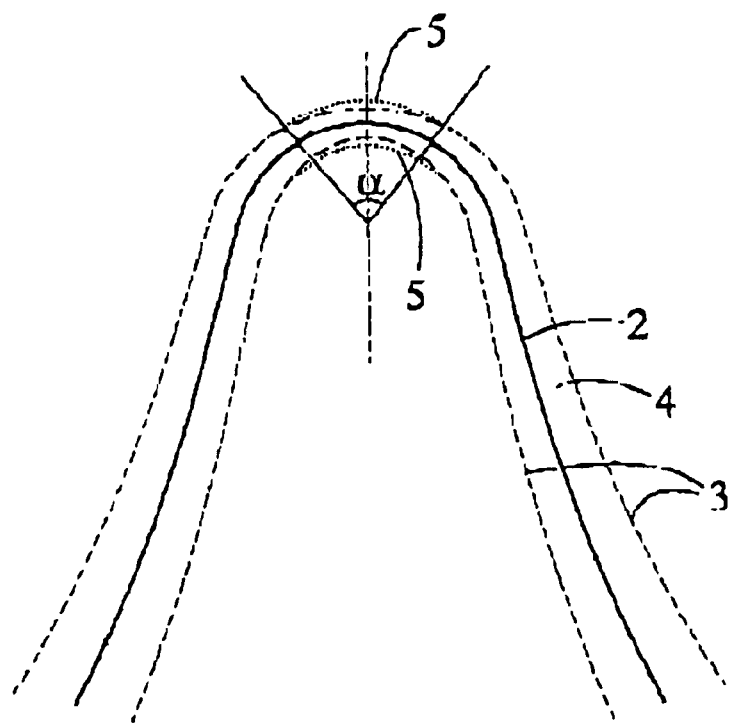
FIG. 2 shows with broken lines the layer of the dental arch that is sharply imaged with the conventional method, and with dotted lines the increase in the sharp layer thickness obtained with the invention in the sector in the front area of the dental arch.

In the panoramic dental X-raying shown in FIG. 2, the sharply imaged layer simulates the dental arch 1 of FIG. 1. The unbroken line 2 in FIG. 2 indicates the central line in the sharp layer on which the spots are projected ideally as spots to the recorder. The broken lines 3 delimit the sharp layer 4, whose spots are projected to the recorder as lines with a length equalling maximally a specific permissible extension maximum. With the conventional method, in which the imaging radius, i.e. the distance between the rotational axis of the arm and the point of the teeth to be X-rayed, is shortest in the front area of the dental arch, the sharp layer 4 narrows in this area as shown in FIG. 2. According to the invention, this narrowing is compensated for as below by an increase in the thickness of the sharp layer in the front area of the dental arch as shown with dotted lines 5 in FIG. 2. The sharp layer has been increased, as in the figure, on both sides of the central normal to the dental arch in a sector with a central angle α of about 70°.

Figure 3:
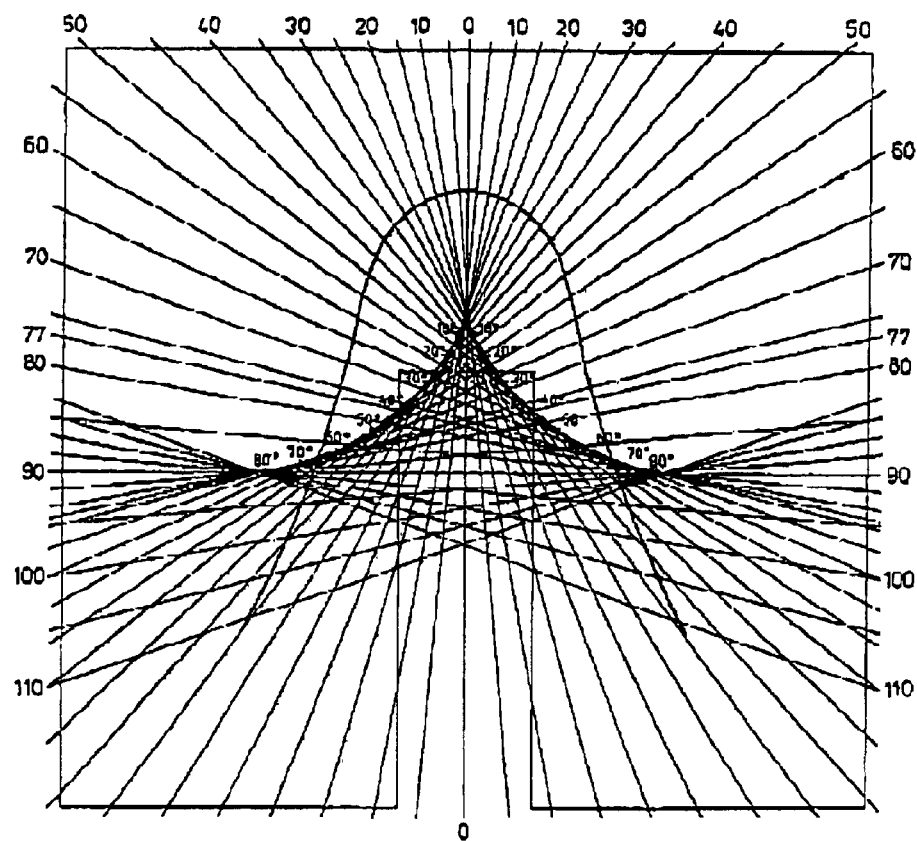
FIG. 3 shows the dental arch with one single line and the movement of the axis of rotation of the arm and the directions of the X-ray beam during the panoramic X-raying process.

FIG. 3 shows how the rotational axis of the arm of the X-raying apparatus is shifted and the direction of the X-ray beam changes in panoramic X-raying, where the sharp layer of the dental arch is imaged as shown in FIG. 2. The central line 2 of the sharp layer of the dental arch that is ideally projected to the recorder has been drawn in FIG. 3. The varying imaging directions, i,e. the directions of the X-ray beam, are indicated with lines at specific angles to the central normal to the dental arch, the angle being marked as 0°. In this context, it should be noted that the imaging direction changes are sliding during the imaging period. As the imaging starts, the rotational axis of the arm is located on the right side of the dental arch, at the location marked with 80°. The imaging starts from the left-hand side of the dental arch with the X-ray beam at 110°, from where the beam rotates to an 80° direction by turning the axis, without the axis being dislodged. After this, while the X-ray beam goes on rotating, the axis of rotation is shifted so as to follow the curved path shown with degrees in the figure, within the dental arch, while approaching the front area of the arch. The purpose of this movement is to carry out X-raying that is as orthogonal as possible, in which the X-ray beam impinges on the dental arch in a direction that is as perpendicular as possible, especially in the front area of the arch.

After the axis of rotation of the arm has reached the culmination of its curved movement on the central normal to the dental arch, where the X-ray beam is at a 0° angle, i.e. the X-ray beam joins the central normal to the arch, the direction of movement of the axis changes while the X-raying moves to the right-hand side of the dental arch. Then the axis starts drawing away from the arch spot to be imaged and follows a curved path marked with degrees in the figure, moving to the left and finally outside the dental arch, where the axis stops, while still continuing to rotate in order to accomplish the X-raying of the right-hand side of the teeth.

In the panoramic X-raying of FIG. 3 explained above, which optimises the aim of orthogonal imaging and minimises the shifting of the axis of rotation, the imaging radius is shortest in the front area of the dental arch, which would result in a decrease in the width of the sharp layer (broken lines 3) shown in FIG. 2, unless the actions of the invention were taken to increase the sharp layer in this area.

Figure 4:
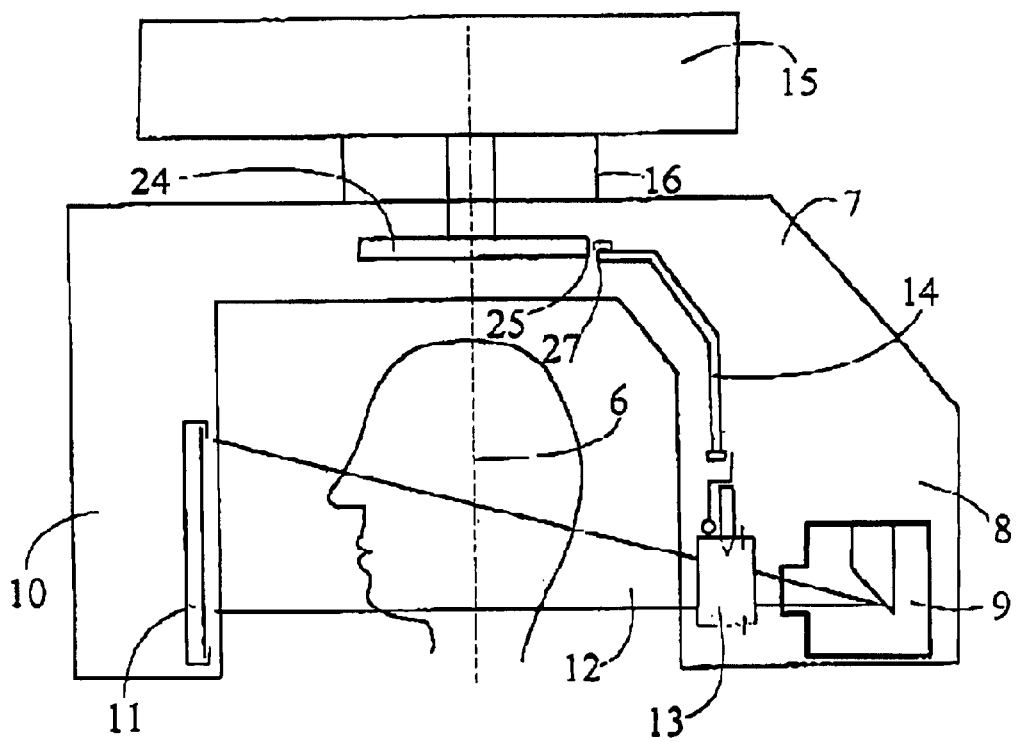
FIG. 4 is a schematic side view of a panoramic X-raying apparatus of the invention.
Figure 5:
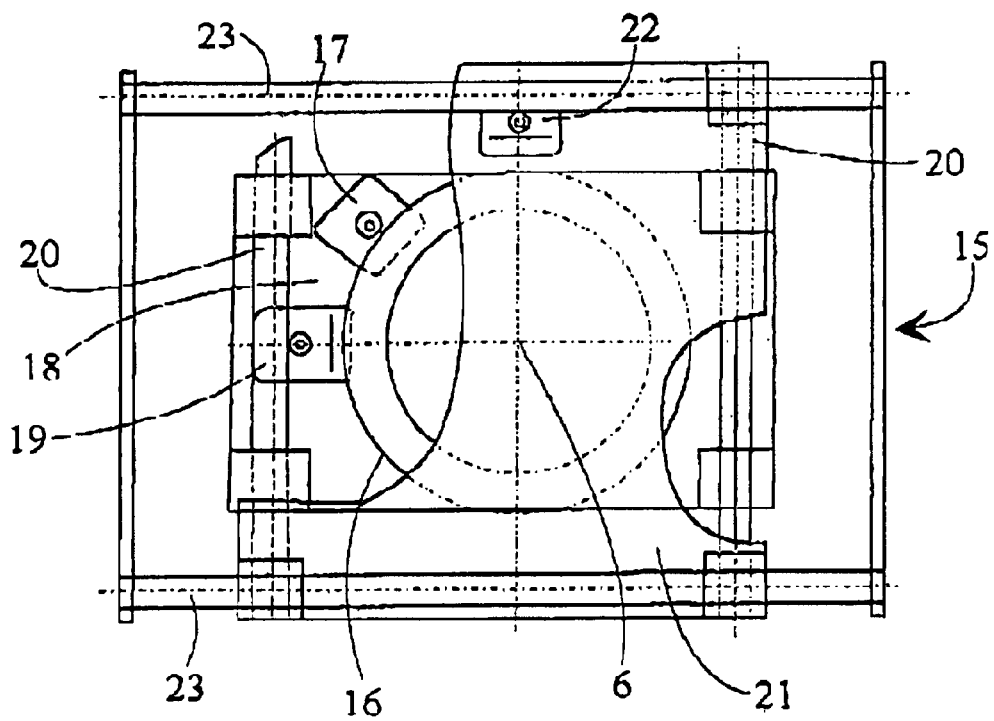
FIG. 5 is a top view of the suspension of the rotational axis of the apparatus of FIG. 4.

FIGS. 4 and 5 are schematic views of the X-raying apparatus of the invention comprising an arm 7 which rotates about an axis of rotation 6, having an X-ray radiation source 9 disposed at one end and an image recorder 11 disposed at the other end. The source of radiation 9 produces an X-ray beam 12, which is shaped with a shutter 13 and which, having passed through the patient's teeth, impinges on the recorder 11, which may consist of e.g. a CCD detector, a CMOS detector, an image plate or an X-ray film. The shutter 23 has a narrow vertical aperture, through which the X-ray beam 12 passes and which is disposed to decrease and increase in width during the X-raying session under the control of a mechanism 14, which coordinates the aperture with the rotational movement of the axis 6.

FIG. 5 shows the arm suspension mechanism 15, which allows the arm 7 to rotate about its axis 6 and the axis to be shifted during the X-raying. The arm 7 is suspended from a tubular suspension arm 16, whose central axis forms the axis of rotation 6 of the arm and which is rotatable with a step motor 17. The tubular suspension arm 16 is pivoted in a plate 18, which can be moved by means of the step motor 19 with two aligned rod guides 20. These rod guides 20, in turn, are fastened to a second plate 21, which can be moved by a step motor 22 with aligned rod guides 23 perpendicular to the rods 22 mentioned above. This provision allows the axis of rotation 6 of the arm to be freely shifted to any location in the plane determined by the rod guides 20, 23 within the play allowed by the rods.

Figure 6:
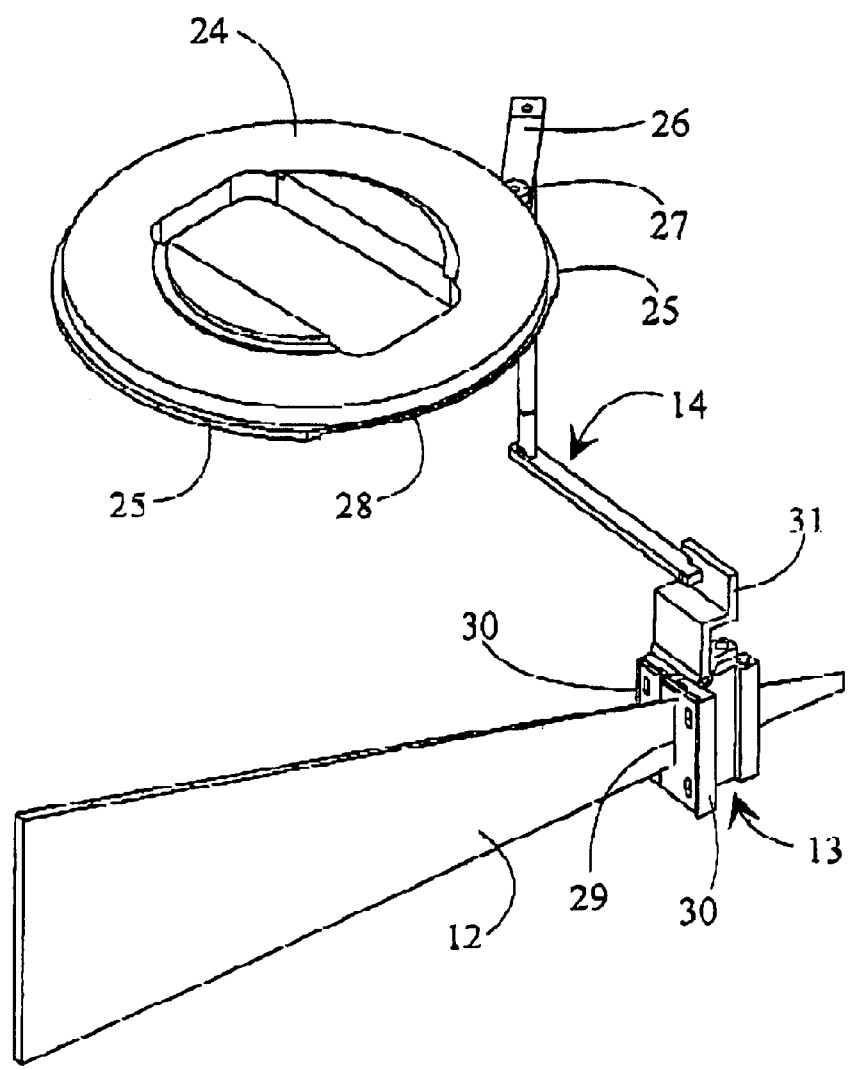
FIG. 6 is an oblique front view of the X-ray beam shutter included in the apparatus of FIG. 4 and the mechanism that connects it to the rotational axis of the arm and FIG. 7 is a back view of the arrangement of FIG. 6.
Figure 7:
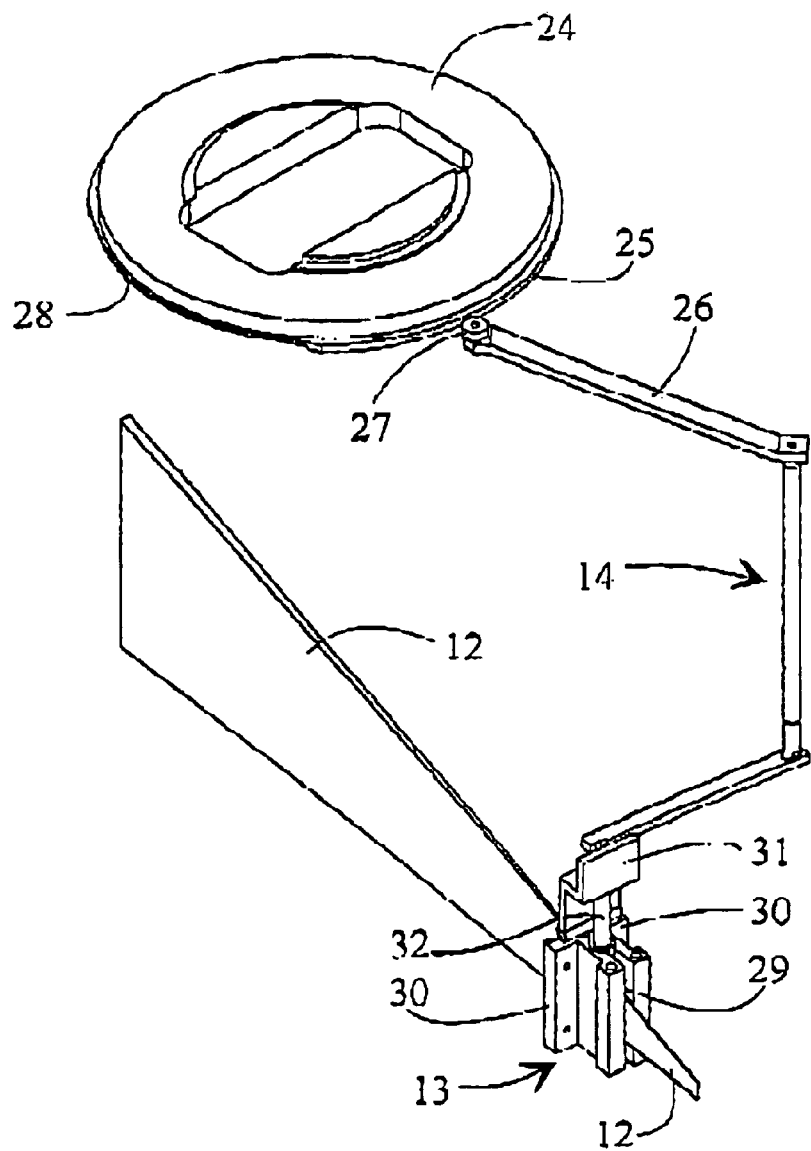

FIGS. 6 and 7 show details of the shutter 13 of the X-ray beam 12 and the mechanism 14 that adjusts the shutter in coordination with the rotational movement of the arm 7. The suspension means 15 include a stationary disc 24, the end 27 of the connecting rod 26 included in the connecting mechanism 14 being adapted to follow the circumference 25 of the disc. It appears from the figure that the circumference of the disc 24 has been milled in the sector 28, which corresponds to the X-raying of the front area of the dental arch during the rotation of the arm. In other words, the end 27 of the arm 26 approaches the center of the disc 24 on the axis of rotation 6 as the X-ray beam enters the front area of the dental arch, and draws away from this again as the X-ray beam leaves this area. The displacements of the arm end 27 are transmitted through the mechanism 14 to the shutter 13, where the aperture 29, which allows the X-ray beam 12 to pass through, is located between two mutually reciprocating parts 30, as the X-raying proceeds to the front area of the dental arch. The connecting mechanism 14 comprises interlinked arms which turn the part 31, which shifts the pin 32, who has a conical lower end and is surrounded by a stop spring (not shown). The movement of the conical end of the pin 32 brings the parts 30 into movement. When the parts 30 approach each other, the aperture 29 between the parts is narrowed. This results in a decrease in the width of the X-ray beam 12 controlled by the aperture 29. Similarly, when the X-raying moves away from the front area of the arch, the mechanism 14 pushes the parts 30 apart, and then the aperture 29 and the X-ray beam 12 become wider. In accordance with the invention, the decreased width of the X-ray beam 12 in the front area of the dental arch results in an increase in the thickness of the sharply imaged layer in this area.

It is obvious to those skilled in the art that the various embodiments of the invention are not limited to the one given as an example above, but may vary within the scope of the accompanying claims. The design of the shutter of the X-ray beam and the operation of the mechanism controlling the aperture width may especially differ from those described above. The mechanical control described above can be replaced by for instance a timer-operated shutter. There are also numerous optional embodiments of the parts that delimit the aperture immediately, and the invention does not set any limits in this respect.

What is claimed is:

1. A panoramic dental X-raying method, comprising emitting a substantially constant intensity X-ray beam (12) from a radiation source (9) provided in a rotating arm (7), guiding said beam through the dental arch (1) to a recorder (11) disposed opposite the radiation source in the arm in order to form an image, rotating the arm so as to form an image of substantially the entire width of the dental arch, limiting the X-ray beam (12) by a shutter (13) in the front area of the dental arch (1) as compared to the two sides of the arch, in order to increase in said front area the thickness of the layer (4) of which a sharp image is formed, and retarding the movement of the X-ray beam (12) in said front area of the dental arch (1) compared to the two sides of the arch.

2. A method as defined in claim 1, wherein narrowing of the X-ray beam and retardation of its movement are performed concomitantly to achieve a substantially constant exposure of the dental arch to X-rays through the entire length of the arch.

3. A method as defined in claim 2, wherein the X-ray beam is first narrowed and then widened by sliding movements of the shutter, accompanied by simultaneous gradual retardation and acceleration of the movement of the X-ray beam so as to subject the arch to a substantially constant exposure to X-rays through the entire length of the arch.

4. A method as defined in claim 1, wherein the X-ray beam (12) is narrowed in a sector of the dental arch (1) having a central angle of about 60–80°.

5. A method as defined in claim 4, wherein the movement of the X-ray beam is retarded in a sector of the dental arch having a central angle of about 60–80°.

6. A method as defined in claim 1, wherein the maximal retardation of the movement of the X-ray beam in the front area is 40–60% as compared to the sides of the arch.

7. A method as defined in claim 1, wherein the X-ray beam (12) is narrowed in the front area of the dental arch (1) so as to increase the thickness of the sharp layer (4) by 50% or more as a result of the decreased width.

8. A method as defined in claim 7, wherein the thickness of the sharp layer (4) is set at least about 1.5 cm in the front area of the dental arch (1).

9. A method as defined in claim 1, wherein the shutter (13) comprises an elongated aperture (29), which allows radiation to pass through and whose width is decreased and increased under mechanical control of the rotational movement of the arm (7).

* * * * *